United States Patent [19]

Kalopissis et al.

[11] 3,966,722

[45] *June 29, 1976

[54] INDAMINES FOR DYEING KERATINOUS FIBERS

[75] Inventors: Gregoire Kalopissis, Paris; Andree Bugaut, Boulogne-sur-Seine; Francoise Estradier, Paris, all of France

[73] Assignee: L'Oreal, Paris, France

[ * ] Notice: The portion of the term of this patent subsequent to July 31, 1990, has been disclaimed.

[22] Filed: May 16, 1973

[21] Appl. No.: 360,741

Related U.S. Application Data

[60] Division of Ser. No. 161,887, July 12, 1971, Pat. No. 3,758,268, which is a continuation-in-part of Ser. No. 52,739, July 6, 1970, Pat. No. 3,677,690.

[30] Foreign Application Priority Data

July 17, 1969  France ............................. 69.59119
July 17, 1970  France ............................. 70.61354
Jan. 15, 1971  France ............................. 71.62429

[52] U.S. Cl. .................................. 260/244 R; 8/10
[51] Int. Cl.$^2$ .............. C07D 265/00; C07D 273/00; C07D 295/00
[58] Field of Search ................................... 260/244

[56] References Cited

UNITED STATES PATENTS 3,600,386  8/1971  Levitt ................................. 260/244
3,749,716  7/1973  Kalopissis et al. ................... 260/244

*Primary Examiner*—Norman A. Drezin
*Assistant Examiner*—D. W. Robinson
*Attorney, Agent, or Firm*—Cushman, Darby & Cushman

[57] ABSTRACT

The invention pertains to indamines and salts thereof which are usefully employed in a dye composition for coloring keratinous fibers, especially human hair and in hair setting lotions which also includes a film-forming cosmetic resin.

15 Claims, No Drawings

INDAMINES FOR DYEING KERATINOUS FIBERS

This is a division of application Ser. No. 161,887, filed July 12, 1971, now U.S. Pat. No. 3,758,268, which in turn is a continuation-in-part of Ser. No. 52,739 filed July 6, 1970, now U.S. Pat. No. 3,677,690.

The present invention relates in one embodiment to a novel indamine and a process for preparing the same and to a novel cosmetic composition containing said indamine for dyeing keratinic fiber such as human hair. More specifically, the present invention relates to a method for preparing and a use of a novel indamine having the formula:

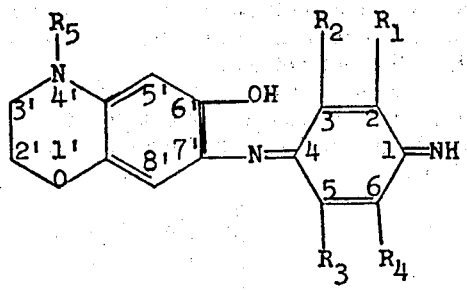

wherein $R_1$, $R_2$, $R_3$ and $R_4$ each represent hydrogen, halogen, lower alkyl having 1-4 carbon atoms and lower alkoxy containing from 1 to 4 carbon atoms, and $R_5$ represents hydrogen or lower alkyl having 1-4 carbon atoms. This formula does not exclude the tautomeric forms.

The novel indamines of this invention can be prepared by condensing a paraphenylenediamine having the formula:

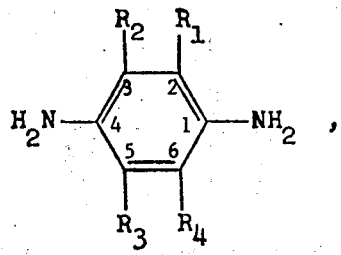

wherein $R_1$, $R_2$, $R_3$ and $R_4$ have the meanings indicated above, on a 6-hydroxy phenomorpholine having the formula:

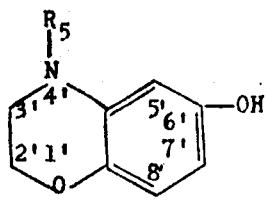

wherein $R_5$ has the meaning given above. Said paraphenylene diamine and/or 6-hydroxy phenomorpholine can also be in the form of a salt such as hydrochloride, hydrobromide or sulfate. This condensation reaction can be performed in an aqueous, aqueous acetone or aqueous alcoholic medium having a pH equal to or greater than 8 and as high as 12, in the presence of an oxidizing agent, and at a temperature between 0° and 50°C.

The oxidizing agent used in this reaction can be hydrogen peroxide or potassium persulfate. When the oxidizing agent is hydrogen peroxide, it is present generally in amounts of about 5–20 times the stoichiometric requirement, and when the oxidizing agent employed is potassium persulfate, it is present in amounts of about 1–2 times the stoichiometric requirements. The reaction medium can be made alkaline, preferably by the addition thereto of ammonia, although other alkalinizing agents such as NaOH and KOH can also be employed.

The paraphenylenediamine used in the preparation of the indamines according to the present invention can be, for example, paraphenylenediamine, paratolylenediamine, 2,5-diamino anisole, 2,5-diamino chlorobenzene, 2-methoxy 5-methyl paraphenylenediamine, 2,6-dimethyl 3-methoxy paraphenylenendiamine and 1,4-diamino durene. The mole ratio of paraphenylenediamine to the 6 hydroxy phenomorpholine in the condensation reaction can vary between about 3:1 to 0.5:1 and preferably between 1:1 to 2:1.

The novel indamines of the present invention constitute dyes that have a particularly interesting application in dyeing keratinous fibers, particularly human hair.

Thus, an object of the present invention is the provision of a novel coloring agent useful in a dyeing composition for keratinous fibers, characterized by the fact that said coloring agent comprises at least one indamine defined above.

When the dyeing composition of the present invention contains as the sole dyeing agent, one or more indamines described above, the coloration imparted to the keratinous fibers by its use varies from blue to green and from green to blond. The obtained colorations impart glints and very often a pearly glance to the keratin fiber.

However, the dye composition of this invention can also include, in addition to the indamines defined above other dyes ordinarily used for dyeing hair. Representative of such other dyes are, for example, azo, aniline, anthraquinone, azine, oxazine dyes and nitroderivatives of the benzene series. Further, indoanilines, indophenols or indamines other than those defined above can also be used.

The novel compositions of this invention comprise an aqueous or aqueous alcoholic solution of the said indamine, which compositions can be prepared by dissolving in said aqueous or aqueous alcoholic medium one or more of said indamines and, if desired, one or more conventionally employed dyes useful in the coloration of keratin fibers. Additionally, however, the composition of this invention can also contain thickeners and thus be in the form of a cream or gel.

Furthermore, the composition of the present invention can also contain various conventional ingredients usually employed in cosmetic preparations, for example, wetting agents, dispersing agents, swelling agents, penetration agents, softeners or perfumes. It has also been found that the composition of this invention can be in the form of a sprayable aerosol, packaged in a conventional aerosol bomb or can.

When the composition of the present invention is employed as a hair dye composition the pH of the hair dye composition can vary within broad limits and will range generally between about 4–11, and preferably between 7–11. The amount of indamine present in the aqueous or aqueous alcohol solution comprising the dye composition can vary, for instance, depending on the particular indamines present, the color desired, as well as the color of the hair to be dyed. Thus an amount of the indamine effective to produce the desired coloration is employed. Generally this amount ranges between about 0.002 to 1 weight percent of the total aqueous or aqueous alcohol solution and, preferably, between about 0.005–0.5% by weight.

Dyeing of keratinous fibers, in particular human hair, with the dyeing composition of this invention is performed in accordance with conventional dyeing techniques, for instance, by applying the said composition to the fibers to by dyed, permitting the composition to remain in contact with said fibers for a period of about 5–30 minutes and thereafter, rinsing and, if desired, washing, and drying the fibers.

The novel indamines of this invention can also be employed to provide a novel hair setting lotion comprising an admixture of at least one of said indamines defined above and a dilute alcohol solution of at least one cosmetic film forming resin.

Cosmetic resins usefully employed to produce said hair setting lotions include, for instance, polyvinyl-pyrrolidone having a molecular weight ranging from about 10,000 to 700,000, copolymers of crotonic acid-vinyl acetate, for examples 10:90% having a molecular weight of about 45,000-50,000, copolymers of vinyl-pyrrolidone-vinyl acetate wherein the ratio of PVP to PVA can range between, for instance, 50–70:50–30, copolymers of maleic anhydride-butylvinyl ether and the like. These resins are generally used in the proportion of 1 to 3% by weight of the total composition. Further, the indamine content of said hair setting lotion usually ranges between about 0.002 to 1% by weight of the total composition, preferably between about 0.005–0.5 weight percent.

The alcohols suitable for making said hair setting lotions are lower alkanols, preferably, ethanol and isopropanol. These alcohols are used in a proportion of 20 to 50% by weight of the total composition.

The hair setting lotion according to the invention is employed in a conventional manner by applying the same to, preferably, previously washed and rinsed, wet hair, followed by rolling the treated hair on curlers and thereafter drying it.

The present invention also relates to salts of indamines having the formula

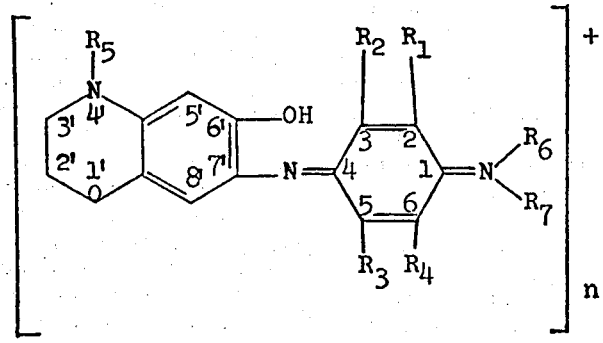

wherein $R_1$, $R_2$, $R_3$ and $R_4$ each independently represent a member selected from the group consisting of hydrogen, halogen, lower alkyl having 1–4 carbon atoms and lower alkoxy having 1–4 carbon atoms, $R_5$ represents a member selected from the group consisting of hydrogen and lower alkyl having 1–4 carbon atoms, $R_6$ and $R_7$ each, independently, represent a member selected from the group consisting of hydrogen, lower alkyl having 1–4 carbon atoms, hydroxy layer alkyl having 1–4 carbon atoms, amino alkyl having 1–4 carbon atoms, acylaminoalkyl wherein the alkyl moiety has 1–4 carbon atoms, morpholinoalkyl wherein the alkyl moiety has 1–4 carbon atoms and piperidinoalkyl wherein the alkyl moiety has 1–4 carbon atoms, $X^{n-}$ is a mono- or divalent anion derived from a mineral or organic acid, and particularly an anion selected from the group consisting of $CH_3CO^-_2$, $Cl^-$, $Br^-$, $(Cl_3Zn)-$ and $S_2O_8^{--}$ and $n$ is 1–2. This formula does not exclude tautomeric forms thereof.

The salts of the indamine can be obtained according to three different methods.

It is thus that, in the case where it is desired to produce a salt of an indamine where $R_6$ and $R_7$ each represent hydrogen one condenses a quinone diimine having the formula

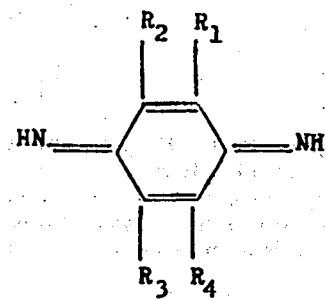

wherein $R_1$, $R_2$, $R_3$ and $R_4$ have the meanings given above on a 6-hydroxy phenomorpholine having the formula

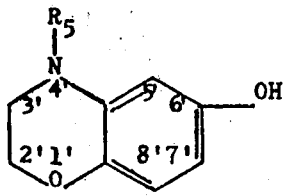

wherein $R_5$ has the meaning given above.

Representative quinone diimines usefully employed in this condensation reaction include 2-methyl 5-methoxy benzoquinone diimine, 2-methoxy 3,5-dimethyl benzoquinone diimine and 3,5-dimethoxy benzoquinone diimine.

When the salt of the indamine thus produced is not very soluble in water, the above condensation reaction can be carried out in water, either in the presence of an acid corresponding to the salt desired, or preferably in the presence of a water-soluble salt of this acid. It is thus that by condensation in an aqueous medium of a quinone diimine, above, on a phenomorpholine of above, in the presence of ammonium persulfate, there is obtained the persulfate salt of said indamine.

When, on the contrary, the salt of the indamine to be produced is very soluble in water, the condensation reaction is carried out in a solvent such as methylisobutyl ketone or dioxan in the presence of an acid corresponding to the salt desired.

In the second method of preparing the indamine salts, one condenses in an aqueous medium or a hydroacetonic medium a paraphenylene diamine having the formula

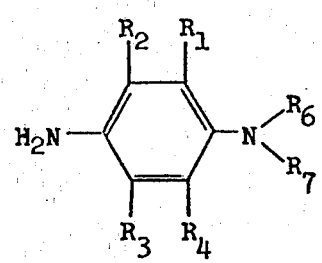

wherein $R_1$, $R_2$, $R_3$, $R_4$, $R_6$ and $R_7$ have the meanings given above, on a 6-hydroxy phenomorpholine, defined above, this condensation reaction being carried out in the presence of a per salt, and preferably in the presence of an alkaline persulfate, such as ammonium persulfate. There is thus obtained a persulfate of the indamine which can be, in certain cases, transposed into another salt of this compound.

The third method of preparing the salt of the indamines is applicable in the situation where $R_6$ and $R_7$ both represent lower alkyl radicals or substituted lower alkyl radicals. This third method comprises condensing a paranitrosoaniline having the formula

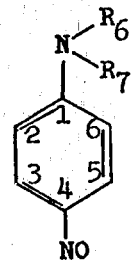

wherein $R_6$ and $R_7$ have the meanings given above on a 6-hydroxy phenomorpholine, as defined above, the condensation reaction being carried out in an alcoholic medium in the presence of zinc chloride. There is thus recovered the double chloride of zinc and indamine.

The salts of the indamines of this invention are dyes which exhibit good solubility in water, lower alkanols such as ethanol and isopropanol and polyols such as butylglycol and polyoxyethylene alcohols, and exhibit strong coloring characteristic in a composition having a pH ranging from 3–10. Accordingly, it is another object of the present invention to provide a composition for dyeing keratinic fibers, particularly human hair, which includes at least one of the above defined indamine salts.

The dye compositions according to the invention can include only as the active coloring agent the indamine salts in which case there is obtained, on white hair, colorations ranging from blue to green, at relatively low application times, in the order of about three minutes, at ambient temperature.

The concentration of the indamine salt in the dye compositions can vary between 0.005–1% by weight, these low concentrations being possible because of the exceptional affinity of the indamine salt for keratinic fibers.

Of course, the dye compositions of this invention containing an indamine salt can also include other dyes such as nitrophenylenediamine dyes, anthraquinone dyes, indophenols, indoanilines or other indamines.

The dye compositions of this invention impart to the keratinic fibers luminous colorations which very often are iridescent and rich in glints, thereby covering or masking the red in reddish chestnut or reddish brown hair so as to obtain deep browns with bronze green glints.

The dye compositions of the present invention containing one or more indamine salts are generally aqueous or aqueous alcoholic solutions of these salts and when an alcohol is included there is employed, preferably, ethanol although other alcohols such as butylglycol or polyoxyethylene alcohols can also be used. Additionally, the dye compositions can contain thickeners and thus be in the form of a cream or gel.

Further, the compositions of the present invention can also include various conventional ingredients usually employed in cosmetic preparations, for example wetting agents, dispersing agents, swelling agents, penetrating agents, softeners and perfumes. It has also been found that the compositions containing these indamine salts can be in the form of a sprayable aerosol, packaged in a conventional aerosol bomb or can.

The pH of the dye compositions containing one or more indamine salts can vary between 3.5–11 and generally between 5–9.

Dyeing of keratinic fibers, and especially human hair, with the dyeing compositions containing the novel indamine salts of this invention, is performed in accordance with conventional dyeing techninques, for instance, by applying the said composition to the fibers to be dyed, permitting the composition to remain in contact with said fibers for a period of about 3–30 minutes and thereafter, rinsing and, is desired, washing and drying the fibers.

The novel indamine salts of this invention can also be employed to provide novel hair setting lotions comprising an admixture of at least one indamine salt defined above an aqueous alcoholic solution of a cosmetic film forming resin.

Cosmetic resins usefully employed to produce hair setting lotions containing the novel indamine salts of this invention include, for instance, polyvinylpyrrolidone having a molecular weight ranging from about 10,000–700,000, copolymers of crotonic acid-vinyl acetate, for instance a 10%:90% copolymer, having a molecular weight ranging from about 45,000–50,000, copolymers of vinylpyrrolidone-vinyl acetate wherein the ratio of PVP to PVA can range between, for instance 50–70:50–30, copolymers of maleic anhydridebutylvinyl ether and the like. These resins are generally used in amounts of 1 to 3% by weight of the total composition. Further, the indamine salt content of said hair setting lotion can range between about 0.005–1% by weight of the total composition.

The alcohols suitable for making said hair setting lotions are lower alkanols, preferably, ethanol and isopropanol. These alcohols are used in amounts of about 20–50% by weight of the total composition.

The pH of the hair setting lotions can vary between 4–10 and preferably between 5–9.

Hair setting lotions according to the present invention which contain as a coloring agent only the above defined indamine salt impart to the hair extremely luminous colorations, rich in pearlescent and iridescent glints, a characteristic long desired in the cosmetic field. These compositions effectively mask the red in reddish chestnut or reddish brown hair, imparting thereto bronze glints.

The hair setting lotions of this invention can also include other coloring agents or dyes such as nitrophenylenediamine dyes, anthraquinone dyes, indoanilines, indophenols or other indamines.

The hair setting lotions are employed in a conventional manner by applying the same to, preferably, previously washed and rinsed, wet hair, followed by rolling the treated hair on curlers and thereafter dyeing it.

The following examples are given to illustrate the present invention. The temperatures indicated in the examples are expressed in degrees Celsius and unless otherwise specifically stated, all parts and percentages are by weight.

EXAMPLE 1

N-[(6'-hydroxy 1'-oxa 4'-aza 1',2',3',4'-tetrahydro) 7'-naphthyl] 2-methyl benzoquinonediimine monohydrate is prepared according to the following reaction:

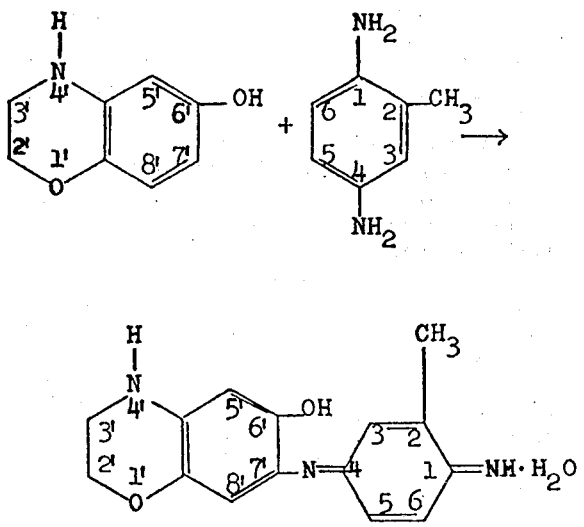

0.06 mole (9.06 g) of 6-hydroxy phenomorpholine is dissolved in 600 cm³ of water. To this solution there are added 180 cm³ of ammonia at 22° Be, 750 cm³ of 20-volume hydrogen peroxide and a solution of 0.12 mole (14.64 g) of paratolylenediamine in 600 cm³ of water. The resulting reaction mixture is allowed to stand for four hours at ambient temperature and thereafter 6.5 g of crystallized indamine, identified above, in monohydrate form is isolated by filtering off the reaction mass. After recrystallization of the indamine crystals in a dimethylformamide-water mixture, the resulting product exhibited a melting point of 258°.

| Analysis | Calculated for $C_{15}H_{15}N_3O_2 \cdot H_2O$ | Found | |
|---|---|---|---|
| C % | 62.71 | 61.81 | 62.05 |
| H % | 5.92 | 5.98 | 6.02 |
| N % | 14.63 | 14.59 | 14.79 |

EXAMPLE 2

N-[(6'-hydroxy 1'-oxa 4'-aza 1',2',3',4'-tetrahydro) 7'-naphthyl] 3-methoxy benzoquinonediimine monohydrate is prepared in accordance with the following reaction:

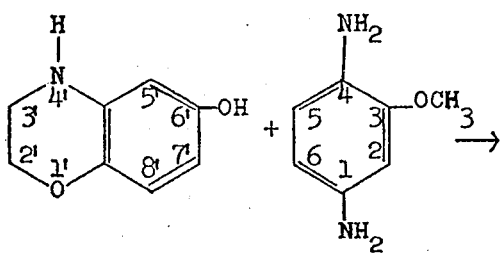

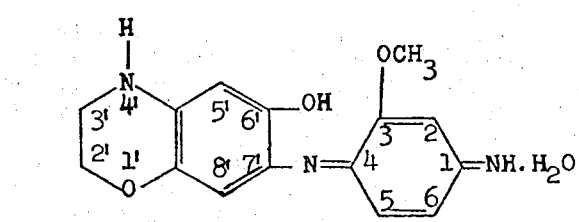

0.025 mole (5.27 g) of methoxyparaphenylenediamine dichlorohydrate is dissolved in 200 cm³ of water. The pH of this solution is then adjusted to a pH of 8 by adding ammonia thereto. To this alkaline solution there is immediately added 0.02 mole (3.02 g) of 6-hydroxy phenomorpholine, previously dissolved in 200 cm³ of water. To this resulting mixture there are added 90 cm³ of ammonia at 22° Be and 260 cm³ of 20-volume hydrogen peroxide. This resulting reaction mixture is then permitted to stand for 2 hours at ambient temperature. The reaction mixture is then filtered off and there is obtained 3.8 g of crystallized indamine in monohydrate form which, after washing with water and recrystallization in a dimethylformamide-water mixture, exhibits a melting point of 216°.

| Analysis | Calculated for $C_{15}H_{15}N_3O_3 \cdot H_2O$ | Found | |
|---|---|---|---|
| C % | 59.40 | 58.88 | 59.07 |
| H % | 5.61 | 5.54 | 5.52 |
| N % | 13.86 | 13.80 | 13.63 |

EXAMPLE 3

N-[(6'-hydroxy 1'-oxa 4'-aza 1',2',3',4'-tetrahydro) 7' naphthyl] 2-methyl 5-methoxy benzoquinone diimine monohydrate is prepared in accordance with the following reaction:

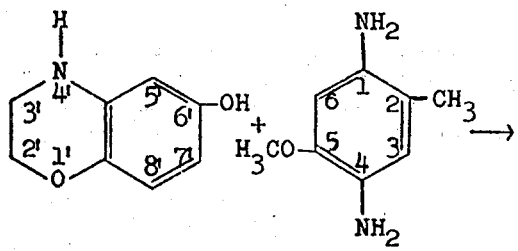

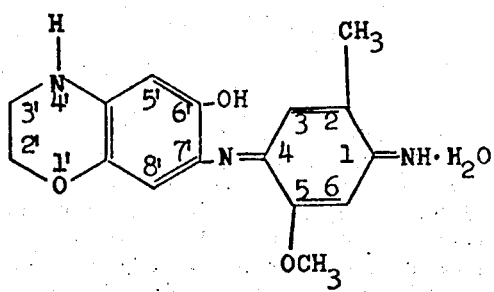

0.03 mole (4.53 g) of 6-hydroxy phenomorpholine is dissolved in 300 cm³ of water. To this solution there are added 90 cm³ ammonia at 22° Be, 350 cm³ of 20-volume hydrogen peroxide and 0.0375 mole (5.7 g) of 2-methyl 5-methoxy paraphenylenediamine in a solution which is a mixture of 50 cm³ of water and 300 cm³ of acetone. The resulting reaction mixture is allowed to stand at ambient temperature for three hours. Then 8.1 g of crystallized indamine in monohydrate form are isolated from the reaction mixture by filtering off the same. After recrystallization in a dimethylformamide water mixture, the product exhibited a melting point of 226°.

Molecular weight calculated for $C_{16}H_{17}N_3O_3 \cdot H_2O$: 317.

Molecular weight found by potentiometric dosing in acetic acid by perchloric acid: 323.

| Analysis | Calculated for $C_{16}H_{17}N_3O_3 \cdot H_2O$ | Found | |
|---|---|---|---|
| N % | 13.24 | 13.38 | 13.30 |

EXAMPLE 4

N-[(6'-hydroxy 1'-oxa 4'-aza 1',2',3',4'-tetrahydro) 7'-naphthyl 2,6-dimethyl 5-methoxy] benzoquinonediimine monohydrate prepared in accordance with the following reaction:

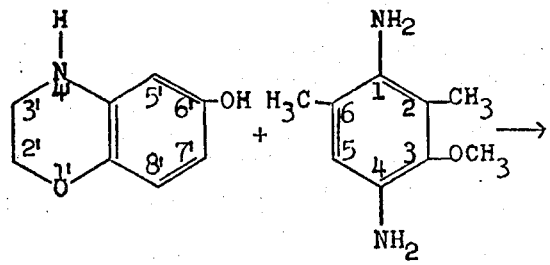

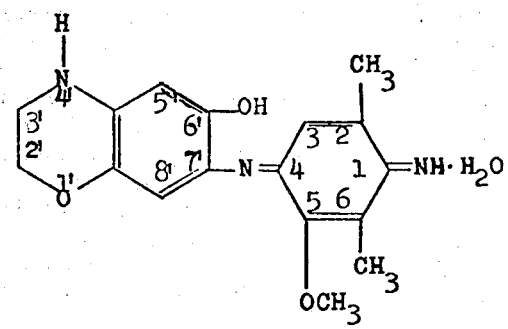

0.02 mole (3.02 g) of 6-hydroxy phenomorpholine is dissolved in 200 cm³ of water. To this solution there are added 0.025 mole (4.1 g) of 2,6-dimethyl 5-methoxy paraphenylenediamine in solution in 200 cm³ of water, 60 cm³ of ammonia at 22° Be and 250 cm³ of 20-volume hydrogen peroxide. The resulting reaction mixture is allowed to stand for two hours at ambient temperature and thereafter 3 g of crystallized indamine in monohydrate form are isolated therefrom by filtering off the reaction mixture. After recrystallization in a dimethylformamide-water mixture, the product exhibited a melting point of 186°.

Molecular weight calculated for $C_{17}H_{19}N_3O_3 \cdot H_2O$: 331.

Molecular weight found by potentiometric dosing in acetic acid by perchloric acid: 333.

| Analysis | Calculated for $C_{17}H_{19}N_3O_3 \cdot H_2O$ | Found | |
|---|---|---|---|
| N % | 12.68 | 12.63 | 12.82 |

EXAMPLE 5

N-[(6'-hydroxy 1'-oxa 4'-aza 1',2',3',4'-tetrahydro) 7'-naphthyl] duroquinone diimine monohydrate is prepared in accordance with the following reaction:

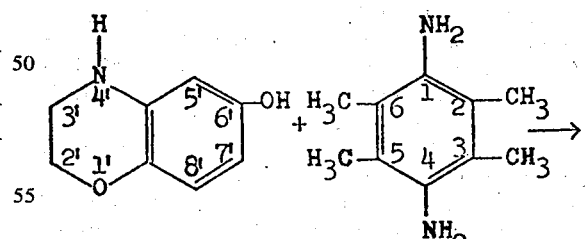

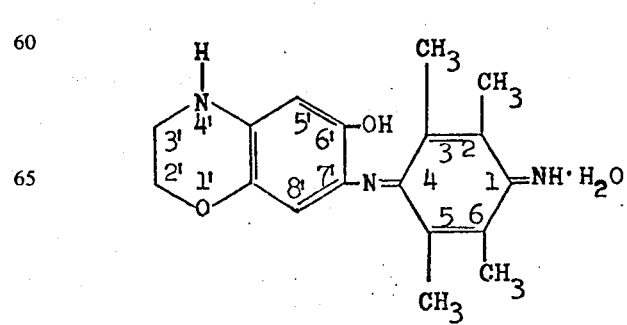

0.005 mole (0.75 g) of 6-hydroxy phenomorpholine is dissolved in 50 cm³ of water. To this solution there are added 15 cm³ of ammonia at 22° Be, 0.01 mole (1.64 g) of 1,4-diamino durene dissolved in a mixture of 30 cm³ of water and 40 cm³ of acetone, and finally 75 cm³ of 20-volume hydrogen peroxide. This resulting reaction mixture is allowed to stand at ambient temperature for five hours. 0.5 g of crystallized indamine identified above in monohydrate form, is isolated by filtering off the reaction mixture. After recrystallization in a dimethylformamide-water mixture, the said indamine exhibited a melting point of 290°.

Molecular weight calculated for $C_{18}H_{21}N_3O_2 \cdot H_2O$: 329.

Molecular weight found by potentiometric dosing in acetic acid by perchloric acid: 334.

| Analysis | Calculated for $C_{18}H_{21}N_3O_2.H_2O$ | Found | |
|---|---|---|---|
| N % | 13.07 | 12.71 | 12.80 |

EXAMPLE 6

N-[(6'-hydroxy 4'-methyl 1'-oxa 4'-aza 1',2',3',4'-tetrahydro) 7'-naphthyl] 3-methoxy 6-methyl benzoquinonediimine monohydrate having the following formula is prepared as follows:

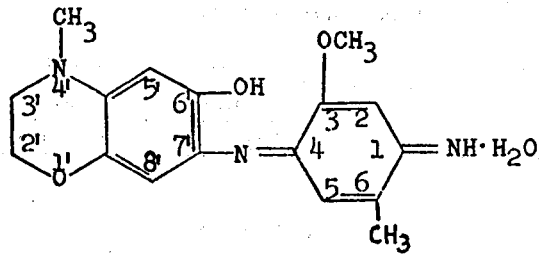

To a solution of 0.0075 mole (1.70 g) of the dihydrochloride of 2-methyl 5-methoxy paraphenylenediamine in 5 cc of water, 7 cc of ammonia (22° Be) and 45 cc acetone, there is added a solution of 0.005 mole (0.825 g) of 6-hydroxy 4-methyl phenomorpholine and finally, with agitation, 35 cc of 20-volume $H_2O_2$. The resulting reaction mixture is allowed to stand for one hour at ambient temperature. The reaction mass is then cooled to 0°C and filtered. The resulting filtrate is washed with water and dried under vacuum, yielding 1.20 grams of crystallized indamine, above, which melts at 166°C.

Molecular weight calculated for $C_{17}H_{19}N_3O_3 \cdot H_2O$: 331.

Molecular weight found by potentiometric dosing in acetic acid by perchloric acid: 325.

| Analysis | Calculated for $C_{17}H_{19}N_3O_3.H_2O$ | Found | |
|---|---|---|---|
| C % | 61.63 | 61.64 | 61.74 |
| H % | 6.34 | 6.36 | 6.46 |

-continued

| Analysis | Calculated for $C_{17}H_{19}N_3O_3.H_2O$ | Found | |
|---|---|---|---|
| N % | 12.69 | 12.49 | 12.53 |

EXAMPLE 7

N-[(6'-hydroxy 4'-methyl 1'-oxa 4'-aza 1',2',3',4'-tetrahydro)7'-naphthyl] 3-methoxy benzoquinonediimine monohydrate having the following formula is prepared as follows:

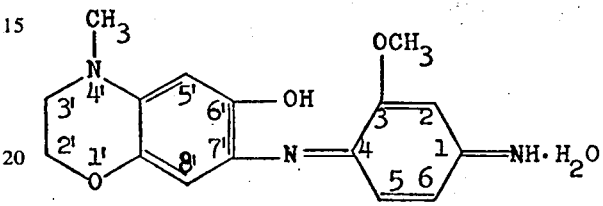

To a solution of 0.01 mole (2.11 g) of the dihydrochloride of methoxy paraphenylene diamine in 10 cc of water to which has been added 7 cc of ammonia (22°Be), there is added a solution of 0.005 mole (0.825 g) of 6-hydroxy 4-methyl phenomorpholine in 10 cc of acetone. Finally there are added to this mixture, with agitation, 26 cc of 20-volume $H_2O_2$. The resulting reaction mass is allowed to stand for 20 minutes at ambient temperature. It is then filtered, the filtrate washed with water and dried under vacuum yielding 0.9 g of the above crystallized indamine which, after recrystallization in a dimethyl formamide-water mixture exhibited a melting point of 174°C.

| Analysis | Calculated for $C_{16}H_{17}N_3O_3.H_2O$ | Found | |
|---|---|---|---|
| C % | 60.55 | 60.60 | 60.42 |
| H % | 6.03 | 5.96 | 6.15 |
| N % | 13.24 | 13.02 | 13.14 |

EXAMPLE 8

N-[(6'-hydroxy 4'-methyl 1'-oxa 4'-aza 1',2',3',4'-tetrahydro)7'-naphthyl] benzoquinone diimine monohydrate having the following formula is prepared as follows:

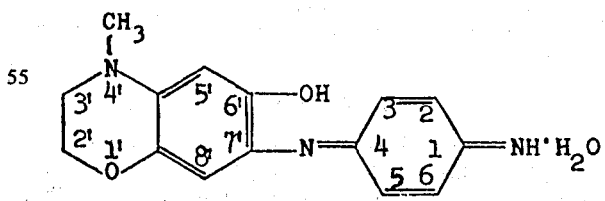

To a solution of 0.02 mole (3.62 g) of the dihydrochloride of paraphenylenediamine in 20 cc of water to which has been added 7.5 cc of ammonia (22°Be), there is added a solution of 0.01 mole (1.65 g) of 6-hydroxy 4-methyl phenomorpholine in 10 cc of acetone. Finally there are added, with agitation, 20 cc of 20-volume $H_2O_2$. The resulting reaction mass is allowed to stand for 30 minutes at ambient temperature and then for 1 hour at 0°C. The reaction mass is filtered and the filtrate washed with water and dried under vacuum, yielding 1.4 g of the above indamine which, after recrystallization in a dimethylformamide-water mixture, exhibited a melting point of 160°C. The resulting indamine is chromatographically pure.

Molecular weight calculated for $C_{15}H_{15}N_3O_2 \cdot H_2O$: 287.

Molecular weight found by potentiometric dosing in dimethylformamide with a 0.1 N isopropanol-methanol solution of tetra-n-butylammonium hydroxide: 278.

EXAMPLE 9

N-[(6'-hydroxy 4'-ethyl 1'-oxa 4'-aza 1',2',3',4'-tetrahydro)7'-naphthyl]3-methoxy 6-methyl benzoquinone diimine monohydrate having the following formula is prepared as follows:

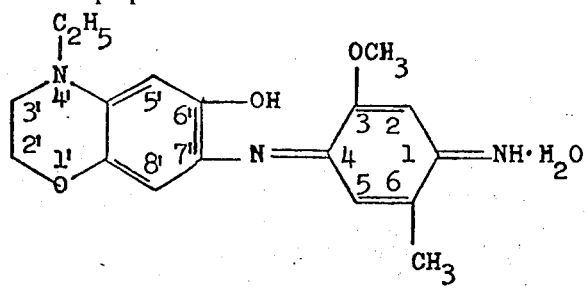

To a solution of 0.015 mole (3.4 g) of the dihydrochloride of 2-methyl 5-methoxy paraphenylene diamine in 10 cc of water, 90 cc of acetone and 14 cc of ammonia (22°Be), there are added 0.01 mole (2.60 g) of the hydrobromide of 6-hydroxy 4-ethyl phenomorpholine in 5 cc of water, 10 cc of acetone and 3 cc of ammonia (22°Be). Finally, to this resulting reaction mixture there are added 70 cc of 20-volume $H_2O_2$. The resulting reaction mass is allowed to stand for 2 hours at ambient temperature. There is then added 20 cc of water. The reaction mass is cooled to 0°C and thereafter filtered, washed with water and dried, yielding 1.70 g of the above indamine. After recrystallization in a dimethylformamide-water mixture, the indamine is chromatographically pure and exhibits a melting point of 136°C.

Molecular weight calculated for $C_{18}H_{21}N_3O_3 \cdot H_2O$: 345.

Molecular weight found by potentiometric dosing in dimethylformamide with a 0.1 N solution in isopropanol-methanol of tetra nbutylammonium hydroxide: 334.

EXAMPLE 10

The zinc and N-[6'-hydroxy 4'-methyl 1'oxa 4'-aza 1',2',3',4'-tetrahydro 7'-naphthyl] N',N'-diethylbenzoquinoneimine iminium double chloride having the following formula is prepared as follows:

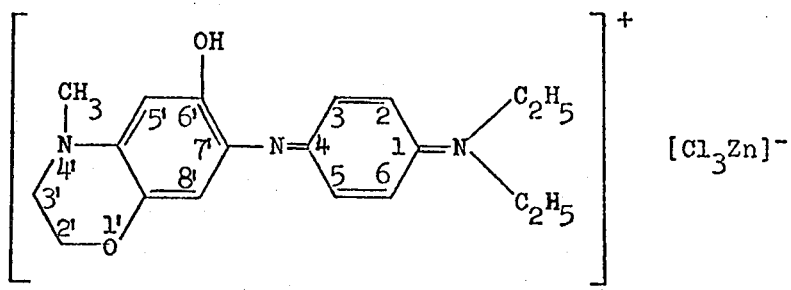

Into 30 cc of absolute ethyl alcohol, there are introduced 0.03 mole (5.35 g) of paranitrosodiethylaniline and 0.03 mole (4.95 g) 6-hydroxy 4-methyl phenomorpholine. To the resulting mixture there is added 0.03 mole (4.08 g) of anhydrous zinc chloride. The mixture is heated to reflux for 30 minutes and thereafter cooled. The precipitate formed is filtered, yielding 10.4 g of the above indamine salt.

% Zn calculated for $[C_{19}H_{22}N_3O_2]^+ [Cl_3Zn]^-$: 13.0
% Zn found (determined under form of ZnO): 12.6

EXAMPLE 11

The zinc and N-[6'-hydroxy 4'-methyl 1'-oxa 4'-aza 1',2',3',4'tetrahydro 7'-naphthyl]N', N'-ethyl β-piperidinoethylbenzoquinoneimine iminium double chloride hydrochloride having the following formula is prepared as follows:

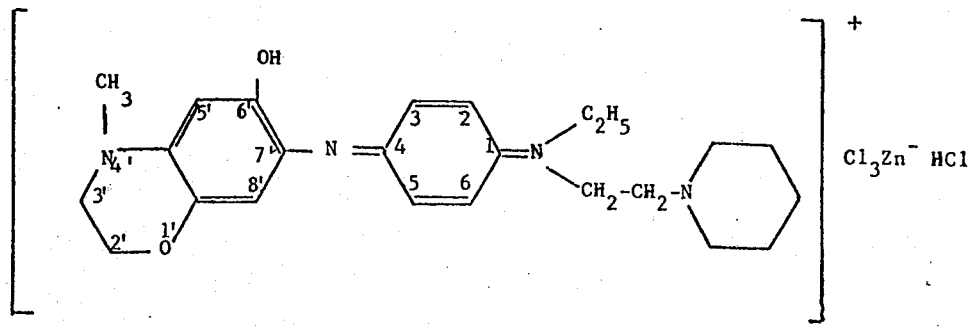

Into 20 cc of absolute ethyl alcohol, there are added 0.005 mole (1.67 g) of the dihydrochloride of paranitroso N-ethyl N-piperidinoethylaniline and 0.005 mole (0.83 g) of 6-hydroxy 4-methyl phenomorpholine. To this resulting mixture there is added 0.8 g of anhydrous zinc chloride. This resulting mixture is heated to reflux for 30 minutes. After cooling, it is filtered and the resulting indamine salt washed with absolute ethyl alcohol and then with ethyl acetate. There is obtained 1.8 g of above indamine salt which is chromatographically pure.

EXAMPLE 12

The zinc and N-[(6'-hydroxy 4'-methyl 1'-oxa 4'-aza 1',2',3',4'-tetrahydro 7'-naphthyl]N', N'-ethyl β-acetylaminoethylbenzoquinoneimine iminium double chloride having the following formula is prepared as follows:

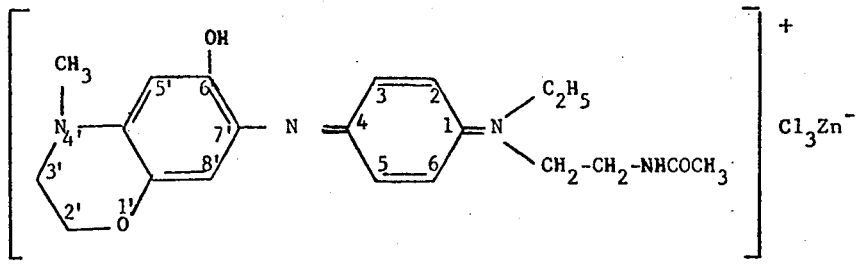

Into 20 cc of absolute ethyl alcohol there are added 0.005 mole (1.18 g) of paranitroso N-ethyl N-β-acetylaminoethylaniline and 0.005 mole (0.83 g) 6-hydroxy 4-methyl phenomorpholine. To this resulting mixture there is added 0.80 g of anhydrous zinc chloride. The mixture is then heated to reflux, with agitation, for 30 minutes. After cooling, the mixture is filtered and the resulting above indamine salt is washed with absolute ethanol and dried under vacuum, yielding 2.2 g of the above salt which is chromatographically pure.

EXAMPLE 13

The zinc and N-[6'-hydroxy 4'methyl 1'-oxa 4'-aza 1',2',3',4'-tetrahydro 7'-naphthyl] N', N'-di-β-hydroxyethylbenzoquinoneimine iminium double chloride having the following formula is prepared as follows:

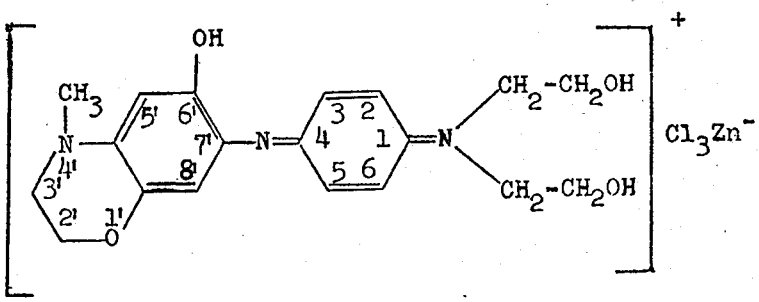

Into 20 cc of absolute ethyl alcohol, there are added 0.005 mole (1.05 g) of paranitroso-N,N-di-β-hydroxyethylaniline and 0.005 mole (0.83 g) of 6-hydroxy 4-methyl phenomorpholine. To this resulting mixture there is added 0.8 g of anhydrous zinc chloride. The mixture is heated to reflux, with agitation, for 30 minutes. After cooling, it is filtered and the thus isolated salt is washed with absolute ethyl alcohol, yielding 2.30 g of the above indamine salt which is chromatographically pure.

EXAMPLE 14

The zinc and N-[(6'-hydroxy 4'-ethyl 1'-oxa 4'-aza 1',2',3',4'-tetrahydro 7'-naphthyl] N',N'-di-β-hydroxyethylbenzoquinoneimine iminium double chloride having the following formula is prepared as follows:

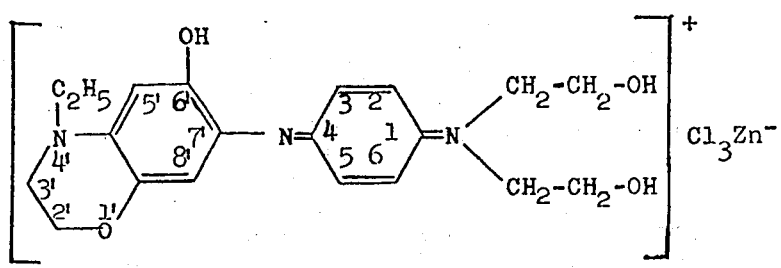

Into 20 cc of absolute ethyl alcohol there are introduced 0.005 mole (1.05 g) of paranitroso-N,N-di-β-hydroxyethylaniline and 0.005 mole (0.90 g) of 6-hydroxy 4-ethyl phenomorpholine. To this resulting mixture there is added 0.8 g of anhydrous zinc chloride. The resulting mixture is heated to reflux, with agitation, for 30 minutes. After cooling the above indamine salt is recovered by filtration and washed with absolute ethyl alcohol, yielding 2.25 g thereof which is chromatographically pure.

EXAMPLE 15

The acetate of N-[6'-hydroxy 1'-oxa 4'-aza 1',2',3',-4'-tetrahydro 7'-naphthyl] 3-methoxy 6-methyl benzoquinoneimine iminium having the following formula is prepared as follows:

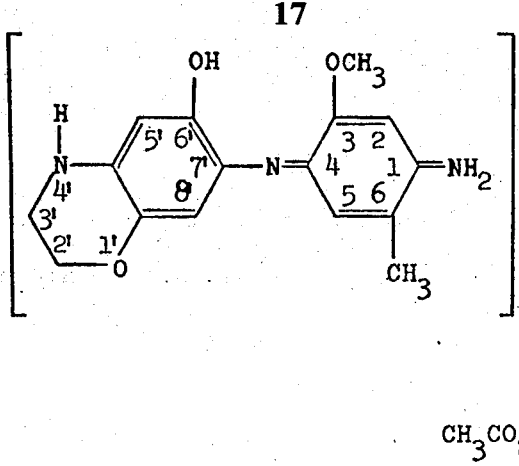

$CH_3CO_2^-$ 0.005 mole (0.75 g) of 2-methyl 5-methoxy benzoquinonediimine is dissolved in 13 cc of methylisobutyl ketone. To this solution there is added 0.005 mole (0.755 g) of 6-hydroxy phenomorpholine in 10 cc of methylisobutylketone to which has been added 0.3 cc of acetic acid. Shortly thereafter the resulting reaction mixture is filtered to isolate the above indamine salt, which after washing with methylisobutylketone and drying yields 0.42 g of the said salt which is chromatographically pure.

Molecular weight calculated for $C_{18}H_{21}N_3O_5$: 359

Molecular weight found by potentiometric dosing in acetic acid with perchloric acid: 345.

EXAMPLE 16

The acetate of N-[(6'-hydroxy 4'-methyl 1'-oxa 4'-aza 1',2',3',4'-tetrahydro 7'-naphthyl] 3-methoxy 6-methyl benzoquinoneimine iminium having the following formula is prepared as follows:

0.005 mole (0.75 g) of 2-methyl 5-methoxy benzoquinonediimine is dissolved in 13 cc of methylisobutyl ketone. To this solution there is added 0.005 mole (0.83 g) of 6-hydroxy 4-methyl phenomorpholine in 10 cc of methylisobutyl ketone to which has been added 0.3 cc of acetic acid. Shortly thereafter the precipitate formed is filtered, washed with a little methylisobutyl ketone and dried, thus yielding 0.40 g of the above indamine salt.

EXAMPLE 17

The persulfate of N-[(6'-hydroxy 1'-oxa 4'-aza 1',-2',3',4'-tetrahydro 7'-naphthyl] 3-methoxy 2,6-dimethyl benzoquinoneimine iminium is prepared as follows:

A first solution is prepared by dissolving 0.005 mole (0.75 g) of 6-hydroxy phenomorpholine in 20 cc of acetone. A second solution is prepared by dissolving 0.0075 mole (1.8 g) of the dihydrochloride of 2-methoxy 3,5-dimethyl paraphenylenediamine in 10 cc of water to which has been added 1.5 cc of ammonia (22°Be). The two solutions are cooled and mixed and to the resulting mixture there is added 2.28 g of ammonium persulfate dissolved in 20 cc of water. The precipitate formed, which is the above indamine salt, is filtered, washed with a little ice water and then with a little acetone and finally dried, yielding 0.7 g of the above indamine salt which is chromatographically pure.

EXAMPLE 18

The persulfate of N-[6'-hydroxy 4'-methyl 1'-oxa 4'-aza 1',2',3',4'-tetrahydro 7'-naphthyl] 3-methoxy 2,6-dimethyl benzoquinoneimine iminium is prepared as follows:

0.005 mole (0.82 g) of 2,6-dimethyl 3-methoxy benzoquinonediimine is dissolved in 11 cc of ice water. To this solution there are immediately added 0.005 mole (0.83 g) of 6-hydroxy 4-methyl phenomorpholine in 3 cc of acetone and 1.5 g of ammonium persulfate dissolved in 4.5 cc of water. The resulting precipitate is filtered off, washed with a little ice water and then with some acetone, yielding 0.65 g of the above indamine salt.

EXAMPLE 19

A hair dye composition, in accordance with this invention, is prepared as follows:

| | | |
|---|---|---|
| The indamine of Example 2 | 0.1 | g |
| Lauryl alcohol oxyethylenated with 10.5 moles of ethylene oxide | 5 | g |
| Water sufficient for | 100 | g |

This dyeing composition solution is applied to 90% gray hair and left in contact therewith for 30 minutes. The hair is then rinsed and shampooed. A green gray shade is obtained.

EXAMPLE 20

A hair setting lotion, in accordance with the present invention, is prepared as follows:

| | | |
|---|---|---|
| Indamine of Example 2 | 0.1 | g |
| Crotonic acid-vinyl acetate copolymer (10%:90%, Mol.wt. 45,000) | 2 | g |
| Ethanol - 96° titer sufficient for | 50 | ° |
| Water sufficient for | 100 | g |

This hair setting lotion is applied to 100% white hair and imparts thereto a dull green hue.

EXAMPLE 21

A hair setting lotion is prepared as follows:

| | | |
|---|---|---|
| The indamine of Example 5 | 0.1 | g |
| Crotonic acid-vinyl acetate copolymer (10%:90%, Mol.wt. 45,000) | 2 | g |
| Isopropanol sufficient for | 50 | ° |
| Water sufficient for | 100 | g |

This hair setting lotion is applied to 100% white hair and imparts thereto a golden blond color.

EXAMPLE 22

A hair dye composition is prepared as follows:

| | | |
|---|---|---|
| The indamine of Example 4 | 0.2 | g |
| Butylglycol | 5 | g |
| Lauryl alcohol oxyethylenated with 10.5 moles of ethylene oxide | 5 | g |
| Water sufficient for | 100 | g |

This hair dye composition is applied to 100% white hair and is permitted to remain in contact therewith for 30 minutes. Thereafter the hair is rinsed and shampooed and a lime coloring is imparted thereto.

EXAMPLE 23

A hair dye composition is prepared as follows:

| | | |
|---|---|---|
| The indamine of Example 4 | 0.1 | g |
| N[(4'-amino 3'-methyl)phenyl] 3-amino 2,6-dimethyl benzoquinoneimine | 0.1 | g |
| Ammonia sufficient for | pH 10.5 | |
| Water sufficient for | 100 | g |

This hair dye composition is applied to white hair and permitted to remain in contact therewith for a period of about 30 minutes. The hair is then rinsed and shampooed and a clear chestnut coloring with slight violet glints is imparted thereto.

EXAMPLE 24

A hair setting lotion is prepared as follows:

| | | |
|---|---|---|
| The indamine of Example 3 | 0.2 | g |
| Crotonic acid-vinyl acetate copolymer (10%:90%, Mol.Wt. 50,000) | 2 | g |
| Ethanol — 96° titer, sufficient for | 50 | ° |
| Water sufficient for | 100 | g |

This hair setting lotion is applied to bleached hair and imparts thereto a blond color with Cyprian green glints.

EXAMPLE 25

The following solution is prepared:

| | | |
|---|---|---|
| The indamine of Example 7 | 0.05 | g |
| Crotonic acid-vinyl acetate copolymer (10%:90%, M.W. 50,000) | 2 | g |
| Ethyl alcohol - 96° titer | 50 | g |
| Water, q.s.p. | 100 | g |
| Triethanolamine, q.s.p. | pH | 7 |

This hair setting lotion is applied to bleached hair and imparts thereto a pale green coloration with golden glints.

EXAMPLE 26

The following solution is prepared:

| | | |
|---|---|---|
| The indamine of Example 7 | 0.2 | g |
| Ethanol, 96° titer | 35 | g |
| Water, q.s.p. | 100 | g |
| Ammonia (22°Be), q.s.p. | pH | 7 |

This solution is applied to bleached hair and is permitted to remain in contact therewith for 20 minutes. After rinsing and shampooing the thus treated hair, there is imparted thereto a golden blond coloring with green glints.

EXAMPLE 27

The following solution is prepared:

| | | |
|---|---|---|
| The indamine of Example 6 | 0.3 | g |
| Ethanol, 96° titer | 50 | g |
| Water, q.s.p. | 100 | g |
| Ammonia (22°Be), q.s.p. | pH | 10.5 |

This solution is applied to 95% naturally white hair and is permitted to remain in contact therewith for 20 minutes. After rinsing and shampooing a pale, silvery green coloration is imparted thereto.

EXAMPLE 28

The following solution is prepared:

| | | |
|---|---|---|
| The indamine of Example 6 | 0.1 | g |
| Crotonic acid-vinyl acetate copolymer (10%:90%, M.W. 45,000–50,000) | 2 | g |
| Ethanol, 96° titer, q.s.p. | 50 | ° |
| Water, q.s.p. | 100 | g |
| Triethanolamine, q.s.p. | pH | 7 |

This hair setting lotion is applied to bleached hair and imparts thereto an almond green coloration.

EXAMPLE 29

The following solution is prepared:

| | | |
|---|---|---|
| The indamine of Example 6 | 0.4 | g |
| Ethanol, 96° titer, q.s.p. | 50 | ° |
| Water, q.s.p. | 100 | g |
| Lactic acid (10% solution), q.s.p. | pH | 4 |

This solution is applied to 95% naturally white hair and is permitted to remain in contact therewith for 15 minutes. After rinsing and shampooing, a pearlescent coloration with very pale luminous green glints is imparted thereto.

EXAMPLE 30

The following solution is prepared:

| | | |
|---|---|---|
| The indamine of Example 6 | 0.1 | g |
| N-[(2',4'-diamino 5'-methoxy) phenyl] benzoquinoneimine | 0.05 | g |
| Ethanol, 96° titer | 50 | g |
| Water, q.s.p. | 100 | g |
| Triethanolamine, q.s.p. | pH | 7 |

This solution is applied to bleached hair and is permitted to remain in contact therewith for 20 minutes. After rinsing and shampooing, there is imparted to the hair a very light iridescent reddish golden coloration.

EXAMPLE 31

The following solution is prepared:

| | |
|---|---|
| The indamine of Example 8 | 0.1 g |
| Crotonic acid-vinyl acetate copolymer (10%:90%, M.W. 45,000–50,000) | 2 g |
| Ethanol, 96° titer, q.s.p. | 50 ° |
| Water, q.s.p. | 100 g |
| Triethanolamine, q.s.p. | pH 7 |

This hair setting lotion is applied to bleached hair and imparts thereto a golden coloration with pale green glints.

EXAMPLE 32

The following solution is prepared:

| | | |
|---|---|---|
| The indamine of Example 8 | 0.4 | g |
| Butyl glycol | 5 | g |
| Lauryl alcohol oxyethylenated with 10.5 moles ethylene oxide | 5 | g |
| Water, q.s.p. | 100 | g |
| The pH of this solution is | 7 | |

This solution is applied to 95% naturally white hair and is permitted to remain in contact therewith for 20 minutes. After rinsing and shampooing, a light bronze coloration is imparted thereto.

EXAMPLE 33

The following solution is prepared:

| | | |
|---|---|---|
| The indamine of Example 6 | 0.2 | g |
| N-[(4'-hydroxy) phenyl] 2,6-dimethyl benzoquinoneimine | 0.05 | g |
| Ethanol, 96° titer | 25 | g |
| Water, q.s.p. | 100 | g |
| Ammonia (22°Be), q.s.p. | pH | 10 |

This solution is applied to 95% naturally white hair and is permitted to remain in contact therewith for 20 minutes. After rinsing and shampooing, a beige coloration with rosewood glints is imparted thereto.

EXAMPLE 34

The following solution is prepared:

| | |
|---|---|
| The indamine of Example 8 | 0.15 g |
| N-[(4'-amino)phenyl] 3-amino 6-methyl benzoquinoneimine | 0.05 g |
| Ethanol, 96° titer, q.s.p. | 35 ° |
| Water, q.s.p. | 100 g |
| Ammonia (22°Be), q.s.p. | pH 8 |

This solution is applied to bleached hair and is permitted to remain in contact therewith for 20 minutes. After rinsing and shampooing, a very luminous pearlescent blond coloration is imparted thereto.

EXAMPLE 35

The following solution is prepared:

| | | |
|---|---|---|
| The indamine of Example 8 | 0.10 | g |
| The acetate of N-[(4'-amino 2-methoxy 5'-methyl)phenyl] 3-amino 6-methyl benzoquinonediimine | 0.025 | g |
| Safranine | 0.0125 | g |
| Ethanol, 96° titer | 25 | g |
| Water, q.s.p. | 100 | g |
| Ammonia (22°Be), q.s.p. | pH | 7 |

This solution is applied to 95% naturally white hair and is permitted to remain in contact therewith for 10 minutes. After rinsing and shampooing, a light blue coloration with silvery glints was imparted thereto.

EXAMPLE 36

The following solution is prepared:

| | |
|---|---|
| The indamine of Example 8 | 0.15 g |
| The hydrochloride of 1-methyl β-aminoethylamino 3-nitro 4-methyl-amino benzene | 0.15 g |
| Crotonic acid-vinyl acetate copolymer (10%:90%, M.W. 45,000–50,000) | 2 g |
| Ethanol, 96° titer | 50 g |
| Water, q.s.p. | 100 g |
| Triethanolamine, q.s.p. | pH 7 |

This hair setting lotion is applied to bleached hair and imparts thereto a pearlescent, purplish, light chestnut coloration.

EXAMPLE 37

The following solution is prepared:

| | |
|---|---|
| The indamine of Example 7 | 0.04 g |
| The zinc and N-[(6'-hydroxy 4'-methyl 1'-oxa 4'-aza 1',2',3',4'-tetrahydro) 7'-naphthyl] N',N'-ethyl β-acetylaminoethyl benzoquinoneimine iminium double chloride | 0.01 g |
| Nitroparaphenylenediamine | 0.03 g |
| Ethanol, 96° titer, q.s.p. | 50 ° |
| Water, q.s.p. | 100 g |
| Triethanolamine, q.s.p. | pH 7 |

This hair setting lotion is applied to bleached hair and imparts thereto a light ashen chestnut coloration having a pearlescent effect.

EXAMPLE 38

The following solution is prepared:

| | |
|---|---|
| The indamine of Example 9 | 0.05 g |
| Crotonic acid-vinyl acetate copolymer (10%:90%, M.W. 45,000–50,000) | 2 g |
| Ethanol, 96° titer, q.s.p. | 50 ° |
| Water, q.s.p. | 100 g |
| Triethanolamine, q.s.p. | pH 7 |

This hair setting lotion is applied to bleached hair and imparts thereto a pearlescent almond green coloration.

EXAMPLE 39

The following solution is prepared:

| | |
|---|---|
| The indamine salt of Example 10 | 0.05 g |
| Crotonic acid-vinyl acetate copolymer (10%:90%, M.W. 45,000–50,000) | 2 g |
| Ethyl alcohol, 96° titer | 50 g |
| Water, q.s.p. | 100 g |
| Triethanolamine, q.s.p. | pH 7 |

This hair setting lotion is applied to 95% white hair and imparts thereto a forget-me-not blue coloration with very silvery glints.

EXAMPLE 40

The following solution is prepared:

| | |
|---|---|
| The indamine salt of Example 10 | 0.2 g |
| Nitroparaphenylene diamine | 0.05 g |
| Ethyl alcohol, 96° titer | 20 g |
| Water, q.s.p. | 100 g |

-continued

| | | |
|---|---|---|
| Ammonia (22°Bé), q.s.p. | pH | 9 |

This solution is applied to 95% naturally white hair and is permitted to remain in contact therewith for 20 minutes at ambient temperature. After rinsing and shampooing the hair, there is imparted thereto a light pearlescent chestnut coloration.

EXAMPLE 41

The following solution is prepared:

| | | |
|---|---|---|
| The indamine salt of Example 11 | 0.05 | g |
| Crotonic acid-vinyl acetate copolymer (10%:90%, M.W. 45,000–50,000) | 2 | g |
| Ethyl alcohol, 96° titer, q.s.p. | 50 | ° |
| Water, q.s.p. | 100 | g |
| Triethanolamine, q.s.p. | pH | 7 |

This hair setting lotion is applied to bleached hair and imparts thereto a forget-me-not blue coloration with silver glints.

EXAMPLE 42

The following solution is prepared:

| | | |
|---|---|---|
| The indamine salt of Example 11 | 0.15 | g |
| N-[(4'-hydroxy)phenyl] 2,6-dimethyl benzoquinoneimine | 0.25 | g |
| Ethyl alcohol, 96° titer | 25 | g |
| Water, q.s.p. | 100 | g |
| Ammonia (22°Bé), q.s.p. | pH | 9.5 |

This solution is applied to 95% naturally white hair and is permitted to remain in contact therewith for 20 minutes. After rinsing and shampooing, there is imparted to the hair a silver gray coloration.

EXAMPLE 43

The following solution is prepared:

| | | |
|---|---|---|
| The indamine salt of Example 11 | 0.10 | g |
| Ethyl alcohol, 96° titer | 25 | g |
| Water, q.s.p. | 100 | g |
| Ammonia (22°Bé), q.s.p. | pH | 9 |

This solution is applied to 95% naturally white hair and is permitted to remain in contact therewith for 20 minutes. After rinsing and shampooing, there is imparted to the hair a deep silver blue coloration.

EXAMPLE 44

The following solution is prepared:

| | | |
|---|---|---|
| The indamine salt of Example 11 | 0.1 | g |
| N-[(2',4'-diamino 5'-methoxy)phenyl] benzoquinoneimine | 0.2 | g |
| Ethyl alcohol, 96° titer | 25 | g |
| Water, q.s.p. | 100 | g |
| Ammonia (22°Bé), q.s.p. | pH | 10 |

This solution is applied to 95% naturally white hair and is permitted to remain in contact therewith for 20 minutes. The hair is then rinsed and washed and there is imparted thereto a rosewood coloration.

EXAMPLE 45

The following solution is prepared:

| | | |
|---|---|---|
| The indamine salt of Example 12 | 0.1 | g |
| Crotonic acid-vinyl acetate copolymer (10%:90%, M.W. 45,000–50,000) | 2 | g |
| Isopropyl alcohol, q.s.p. | 50 | ° |
| Water, q.s.p. | 100 | g |
| Triethanolamine, q.s.p. | pH | 7 |

Triethanolamine, q.s.p. ............ pH 7

This hair setting lotion is applied to bleached hair and imparts thereto a silver blue coloration.

EXAMPLE 46

The following solution is prepared:

| | | |
|---|---|---|
| The indamine salt of Example 12 | 0.1 | g |
| Water, q.s.p. | 100 | g |

This solution, which has a pH of 7 is applied to 95% naturally white hair and is permitted to remain in contact therewith for 20 minutes. The hair is then rinsed and shampooed and there is imparted thereto a blue gray coloration.

EXAMPLE 47

The following solution is prepared:

| | | |
|---|---|---|
| The indamine salt of Example 12 | 0.2 | g |
| Water, q.s.p. | 100 | g |
| Lactic acid (10% solution), q.s.p. | pH | 4 |

This solution is applied to 95% naturally white hair and is permitted to remain in contact therewith for 10 minutes. The hair is then rinsed and shampooed and there is imparted thereto a silver gray coloration with light green glints.

EXAMPLE 48

The following solution is prepared:

| | | |
|---|---|---|
| The indamine salt of Example 12 | 0.025 | g |
| N-[(4'-hydroxy 3',5'-dimethyl)phenyl] 2,6-dimethyl benzoquinoneimine | 0.125 | g |
| Crotonic acid-vinyl acetate copolymer (10%:90%, M.W. 45,000–50,000) | 2 | g |
| Isopropanol, q.s.p. | 50 | ° |
| Water, q.s.p. | 100 | g |
| Triethanolamine, q.s.p. | pH | 7 |

This hair setting lotion is applied to bleached hair and imparts thereto a light violet coloration with pearlescent glints.

EXAMPLE 49

The following solution is prepared:

| | | |
|---|---|---|
| The indamine salt of Example 13 | 0.04 | g |
| N-[(2',4'-diamino 5'-methyl)phenyl] benzoquinoneimine | 0.05 | g |
| Nitroparaphenylene diamine | 0.04 | g |
| Ethyl alcohol, 96° titer, q.s.p. | 40 | ° |
| Water, q.s.p. | 100 | g |
| Ammonia (22°Bé), q.s.p. | pH | 10 |

This solution is applied to 95% naturally white hair and is permitted to remain in contact therewith for 20 minutes. The hair is then rinsed and shampooed and there is imparted thereto a light cinderash chestnut coloration with purplish glints.

EXAMPLE 50

The following solution is prepared:

| | | |
|---|---|---|
| The indamine salt of Example 13 | 0.05 | g |
| N-[(4'-hydroxy)phenyl]3-amino 6-methyl benzoquinoneimine | 0.20 | g |
| Nitroorthophenylenediamine | 0.10 | g |
| Crotonic acid-vinyl acetate copolymer (10%:90%, M.W. 45,000–50,000) | 2 | g |
| Isopropyl alcohol, q.s.p. | 50 | ° |
| Water, q.s.p. | 100 | g |
| Triethanolamine, q.s.p. | pH | 7 |

This hair setting lotion is applied to bleached hair and imparts thereto a light golden bronze coloration.

EXAMPLE 51

The following solution is prepared:

| | | |
|---|---|---|
| The indamine salt of Example 14 | 0.05 | g |
| Crotonic acid-vinyl acetate copolymer (10%:90%, M.W. 45,000–50,000) | 2 | g |
| Ethanol, 96° titer, q.s.p. | 50 | ° |
| Water, q.s.p. | 100 | g |
| Triethanolamine, q.s.p. | pH | 7 |

This hair setting lotion is applied to bleached hair and imparts thereto a very luminous silver blue coloration.

EXAMPLE 52

The following solution is prepared:

| | | |
|---|---|---|
| The indamine salt of Example 15 | 0.1 | g |
| Crotonic acid-vinyl acetate copolymer (10%:90%, M.W. 45,000) | 2 | g |
| Isopropyl alcohol, q.s.p. | 50 | ° |
| Water, q.s.p. | 100 | g |
| Triethanolamine, q.s.p. | pH | 7 |

This hair setting lotion is applied to bleached hair and imparts thereto a very luminous deep blue coloration.

EXAMPLE 53

The following solution is prepared:

| | | |
|---|---|---|
| The indamine salt of Example 15 | 0.02 | g |
| Water, q.s.p. | 100 | g |
| Ammonia (22°Be), q.s.p. | pH | 10 |

This solution is applied to 95% naturally white hair and is permitted to remain in contact therewith for 3 minutes. The hair is then rinsed and shampooed and there is imparted thereto a light blue green coloration with silver glints.

EXAMPLE 54

The following solution is prepared:

| | | |
|---|---|---|
| The indamine salt of Example 15 | 0.025 | g |
| N-[(2',4'-diamino 5'-methoxy)phenyl] benzoquinoneimine | 0.1 | g |
| Crotonic acid-vinyl acetate copolymer (10%:90%, M.W. 45,000) | 2 | g |
| Isopropyl alcohol | 50 | g |
| Water, q.s.p. | 100 | g |
| Triethanolamine, q.s.p. | pH | 7 |

This hair setting lotion is applied to bleached hair and imparts thereto a pearlescent blue gray coloration.

EXAMPLE 55

The following solution is prepared:

| | | |
|---|---|---|
| The indamine salt of Example 15 | 0.2 | g |
| Crotonic acid-vinyl acetate copolymer (10%:90%, M.W. 45,000–50,000) | 2 | g |
| Ethyl alcohol, 96° titer | 50 | g |
| Water, q.s.p. | 100 | g |
| Triethanolamine, q.s.p. | pH | 7 |

This hair setting lotion is applied to bleached hair and imparts thereto a very deep chestnut coloration with bronze green glints.

EXAMPLE 56

The following solution is prepared:

| | | |
|---|---|---|
| The indamine salt of Example 16 | 0.05 | g |
| Crotonic acid-vinyl acetate copolymer (10%:90%, M.W. 50,000) | 2 | g |
| Isopropyl alcohol | 50 | g |
| Water, q.s.p. | 100 | g |
| Triethanolamine, q.s.p. | pH | 7 |

This hair setting lotion is applied to 95% naturally white hair and imparts thereto an emerald green coloration.

EXAMPLE 57

The following solution is prepared:

| | | |
|---|---|---|
| The indamine salt of Example 16 | 0.5 | g |
| Isopropyl alcohol, | 20 | g |
| Water, q.s.p. | 100 | g |
| Lactic acid (1% solution), q.s.p. | pH | 5 |

This solution is applied to 95% naturally white hair and is permitted to remain in contact therewith for 20 minutes. The hair is then rinsed and shampooed and there is imparted thereto a very luminous blue green coloration.

EXAMPLE 58

The following solution is prepared:

| | | |
|---|---|---|
| The indamine salt of Example 17 | 0.05 | g |
| Crotonic acid-vinyl acetate copolymer (10%:90%, M.W. 50,000) | 2 | g |
| Ethyl alcohol, 96° titer | 50 | g |
| Water, q.s.p. | 100 | g |
| Triethanolamine, q.s.p. | pH | 7 |

This hair setting lotion is applied to bleached hair and imparts thereto a periwinkle blue coloration with iridescent glints.

EXAMPLE 59

The following solution is prepared:

| | | |
|---|---|---|
| The indamine salt of Example 18 | 0.15 | g |
| Crotonic acid-vinyl acetate copolymer (10%:90%, M.W. 50,000) | 2 | g |
| Ethyl alcohol, 96° titer | 50 | g |
| Water, q.s.p. | 100 | g |
| Triethanolamine | pH | 7 |

This hair setting solution is applied to bleached hair and imparts thereto a very iridescent deep blue coloration.

EXAMPLE 60

The following solution is prepared:

| | | |
|---|---|---|
| The indamine salt of Example 18 | 0.2 | g |

-continued

| Butylglycol | 5 g |
| Lauryl alcohol oxyethylenated with 10.5 moles ethylene oxide | 5 g |
| Water, q.s.p. | 100 g |

This solution is applied to 95% naturally white hair and is permitted to remain in contact therewith at ambient temperature for 20 minutes. The hair is then rinsed and shampooed and there is imparted thereto a light bluish green coloration.

EXAMPLE 61

The following solution is prepared:

| The indamine of Example 1 | 0.2 g |
| Crotonic acid - vinyl acetate copolymer (10% : 90%, mol. Wt.50,000) | 2 g |
| Ethanol - 96° titer, sufficient for | 50 |
| Water, sufficient for | 100 g |

This hair setting lotion is applied to bleached hair and imparts thereto a light cinderash blond coloration with lime glints.

EXAMPLE 62

The following solution is prepared:

| The indamine of Example 4 | 0.2 g |
| N-[(4-hydroxy) phenyl] 3-acetylamino 6-methyl benzoquinoneimine | 0.2 g |
| Ammonia (22° Be), sufficient for | pH 10 |
| Water, sufficient for | 100 g |

This solution is applied to 95% naturally white hair and is permitted to remain in contact therewith for 30 minutes. After rinsing and shampooing, a cinderash blond with light pink glints was imparted thereto.

What is claimed is:

1. A compound selected from the group consisting of
   1. an indamine having the formula

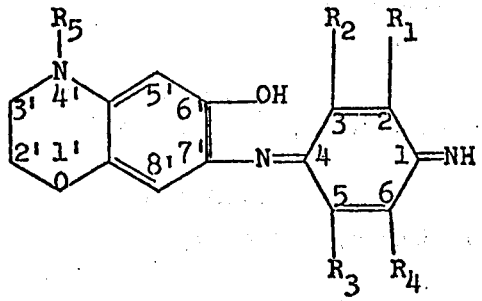

wherein $R_1$, $R_2$, $R_3$ and $R_4$ each, independently, represent a member selected from the group consisting of hydrogen, lower alkyl having 1-4 carbon atoms and lower alkoxy having 1-4 carbon atoms and $R_5$ represents lower alkyl having 1-4 carbon atoms, and
   2. an indamine salt having the formula

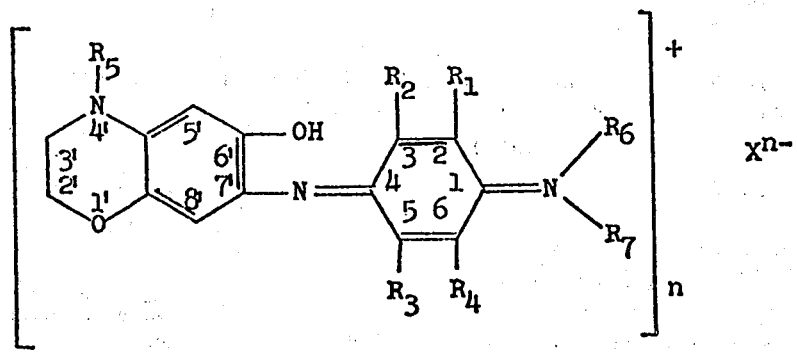

wherein $R_1$, $R_2$, $R_3$ and $R_4$ have the meanings given above, $R_5$ represents a member selected from the group consisting of hydrogen and lower alkyl having 1-4 carbon atoms, $R_6$ and $R_7$ each independently represent a member selected from the group consisting of hydrogen, lower alkyl having 1-4 carbon atoms, hydroxy lower alkyl having 1-4 carbon atoms, acylaminoalkyl wherein the alkyl moiety has 1-4 carbon atoms and piperidinoalkyl wherein the alkyl moiety has 1-4 carbon atoms, $X^{n-}$ is an anion selected from the group consisting of $CH_3CO_2^-$, $(Cl_3Zn)^-$ and $S_2O_8^{--}$ and $n$ is 1-2.

2. A compound having the formula

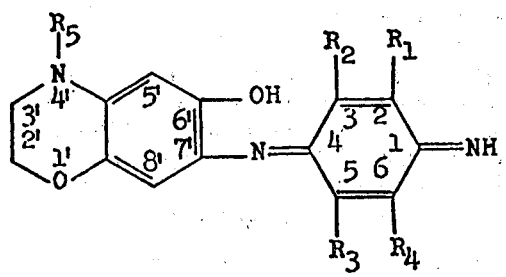

wherein $R_1$, $R_2$, $R_3$ and $R_4$ each, independently, represent a member selected from the group consisting of hydrogen, lower alkyl having 1- 4 carbon atoms and lower alkoxy having 1-4 carbon atoms and $R_5$ represents lower alkyl having 1-4 carbon atoms.

3. The compound of claim 2 wherein $R_5$ is methyl.
4. The compound of claim 2 wherein $R_5$ is ethyl.
5. A compound having the formula

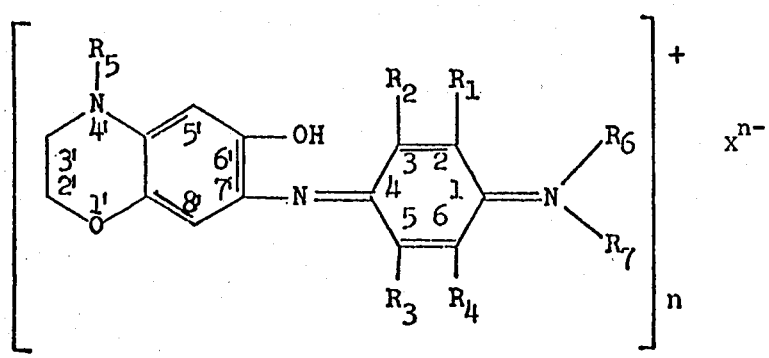

wherein $R_1$, $R_2$, $R_3$ and $R_4$ each, independently, represent a member selected from the group consisting of hydrogen, lower alkyl having 1-4 carbon atoms and lower alkoxy having 1-4 carbon atoms, $R_5$ represents a member selected from the group consisting of hydrogen and lower alkyl having 1-4 carbon atoms, $R_6$ and $R_7$ each, independently, represent a member selected from the group consisting of hydrogen, lower alkyl having 1-4 carbon atoms, hydroxy lower alkyl having 1-4 carbon atoms, acylaminoalkyl wherein the alkyl moiety has 1-4 carbon atoms and piperidinoalkyl wherein the alkyl moiety has 1-4 carbon atoms, $X^{n-}$ is an anion selected from the group consisting of $CH_3CO_2^-$, $(Cl_3Zn)^-$ and $S_2O_8^{--}$ and $n$ is 1-2.

6. The compound of claim 5 wherein $R_5$ is selected from the group consisting of methyl and ethyl.

7. A process for producing a compound having the formula

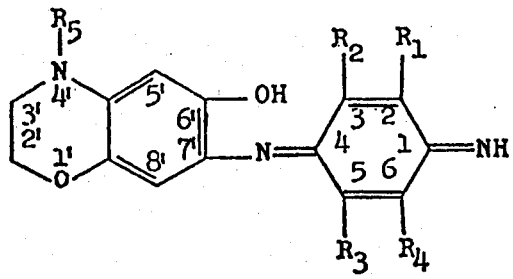

which comprises condensing a paraphenylenediamine having the formula

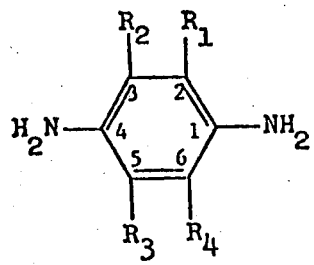

wherein $R_1$, $R_2$, $R_3$ and $R_4$ each independently represent a member selected from the group consisting of hydrogen, lower alkyl having 1-4 carbon atoms and lower alkoxy having 1-4 carbon atoms on a 6-hydroxy phenomorpholine having the formula

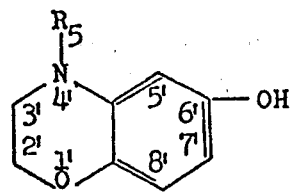

wherein $R_5$ represents lower alkyl having 1-4 carbon atoms, in a medium selected from the group consisting of water, an aqueous alcoholic solution and an aqueous solution of acetone, said medium having a pH of at least about 8 in the presence of an oxidizing agent selected from the group consisting of hydrogen peroxide present in an amount of about 5–20 times the stoichiometric requirement and potassium persulfate present in an amount of about 1–2 times the stoichiometric requirement and at a temperature ranging between 0° and 50°C.

8. The process of claim 7 wherein said paraphenylenediamine is in the form of its hydrochloride.

9. The process of claim 7 wherein said phenomorpholine is in the form of its hydrobromide.

10. The process of claim 7 wherein said phenomorpholine is 6-hydroxy 4-alkyl phenomorpholine.

11. The process of claim 10 wherein said phenomorpholine is 6-hydroxy 4-methyl phenomorpholine.

12. The process of claim 10 wherein said 6-hydroxy 4-alkyl phenomorpholine is 6-hydroxy 4-ethyl phenomorpholine.

13. A process for producing a compound having the formula

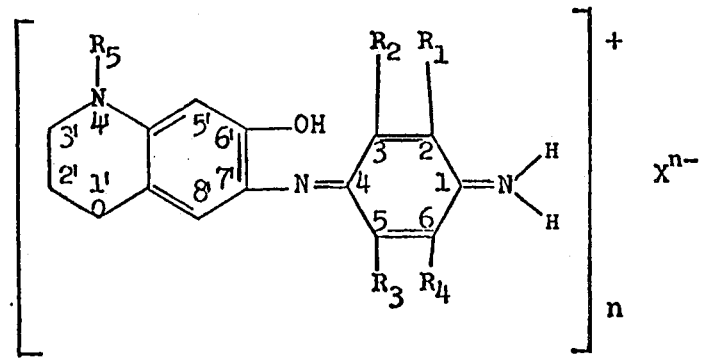

wherein $R_1$, $R_2$, $R_3$ and $R_4$ each, independently, represent a member selected from the group consisting of hydrogen, lower alkyl having 1-4 carbon atoms and lower alkoxy having 1-4 carbon atoms, $R_5$ represents a member selected from the group consisting of hydrogen and lower alkyl having 1-4 carbon atoms, $X^{n-}$ is an anion selected from the group consisting of $CH_3CO_2^-$, and $S_2O_8^{--}$ and $n$ is 1-2, comprising condensing a quinone diimine having the formula

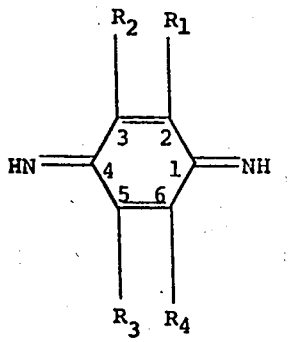

wherein $R_1$, $R_2$, $R_3$ and $R_4$ have the meanings given above on an equimolar amount of 6-hydroxy phenomorpholine having the formula

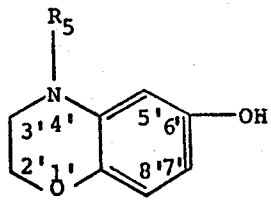

wherein $R_5$ has the meaning given above, in a reaction medium selected from the group consisting of water, methylisobutyl ketone and dioxane, in the presence of a corresponding material having said anion $X^{n-}$ selected from the group consisting of acetic acid and ammonium persulfate.

14. A process for producing a compound having the formula wherein $R_1$, $R_2$, $R_3$ and $R_4$ each, independently, represent a member selected from the group consisting of hydrogen, lower alkyl having 1-4 carbon atoms and lower alkoxy having 1-4 carbon atoms, $R_5$ represents a member selected from the group consisting of hydrogen and lower alkyl having 1-4 carbon atoms, $R_6$ and $R_7$ each, independently, represent a member selected from the group consisting of hydrogen, lower alkyl having 1-4 carbon atoms, hydroxy lower alkyl having 1-4 carbon atoms, acylamino wherein the alkyl moiety has 1-4 carbon atoms and piperidinoalkyl wherein the alkyl moiety has 1-4 carbon atoms, $X^{n-}$ is persulfate, and $n$ is 2, the steps comprising condensing a paraphenylenediamine having the formula

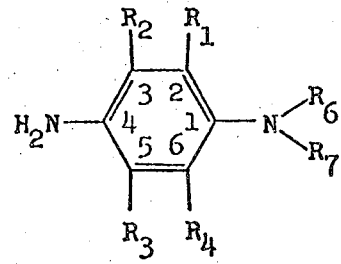

wherein $R_1$, $R_2$, $R_3$, $R_4$, $R_6$ and $R_7$ have the meanings given above on an equimolar amount of a 6-hydroxy phenomorpholine having the formula

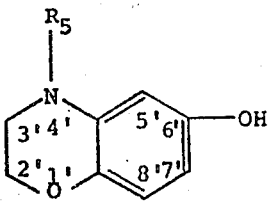

wherein $R_5$ has the meaning given above in an aqueous acetone solution in the presence of ammonium persulfate.

15. A process for producing a compound having the formula

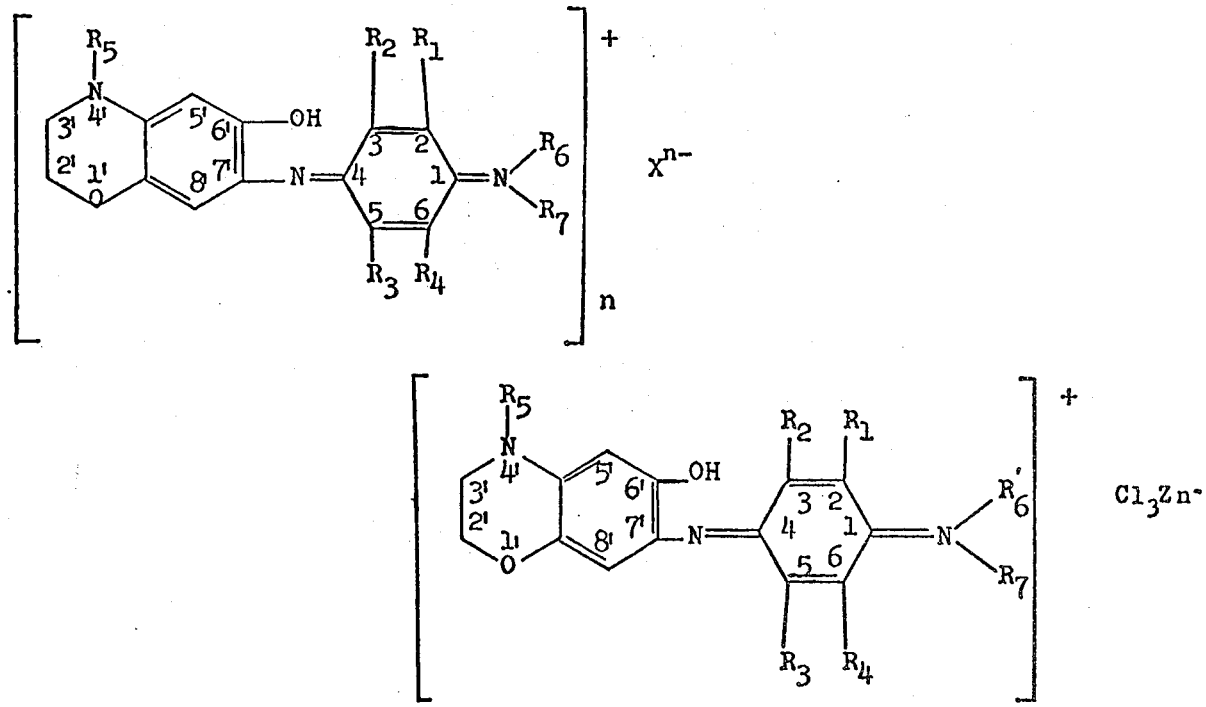

wherein $R_1$, $R_2$, $R_3$ and $R_4$ each, independently, represent a member selected from the group consisting of hydrogen, lower alkyl having 1-4 carbon atoms and lower alkoxy having 1-4 carbon atoms, $R_5$ represents a member selected from the group consisting of hydrogen and lower alkyl having 1-4 carbon atoms, $R_6$ and $R_7$ each, independently, represent a member selected from the group consisting of lower alkyl having 1-4 carbon atoms, hydroxy lower alkyl having 1-4 carbon atoms, acylaminoalkyl wherein the alkyl moiety has 1-4 carbon atoms and piperidinoalkyl wherein the alkyl moiety has 1-4 carbon atoms, the steps comprising condensing a paranitrosoaniline having the formula

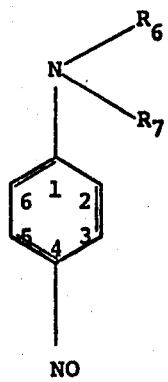

wherein $R_6$ and $R_7$ have the meaning given above on an equimolar amount of a 6-hydroxy phenomorpholine having the formula

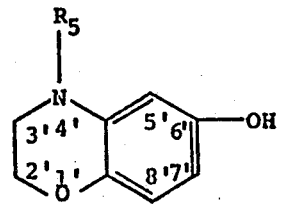

wherein $R_5$ has the meaning given above, in an ethyl alcohol reaction medium heated to reflux with agitation for 30 minutes in the presence of zinc chloride.

* * * * *

UNITED STATES PATENT OFFICE
CERTIFICATE OF CORRECTION

PATENT NO. : 3,966,722
DATED : June 29, 1976
INVENTOR(S) : GREGOIRE KALOPISSIS ET AL.

It is certified that error appears in the above-identified patent and that said Letters Patent are hereby corrected as shown below:

Page 1, under "[30] Foreign Application Priority Data"

all priority rights should be --Luxembourg-- instead of "France"; and another priority application should be listed as follows:

--Jan. 15, 1971   Luxembourg        71.62426--.

Signed and Sealed this

Twenty-eighth Day of September 1976

[SEAL]

Attest:

RUTH C. MASON
Attesting Officer

C. MARSHALL DANN
Commissioner of Patents and Trademarks